United States Patent [19]

Tan et al.

[11] Patent Number: 4,894,475
[45] Date of Patent: Jan. 16, 1990

[54] ALPHA-ACYLOXYKETONE DERIVATIVES

[75] Inventors: Hiroaki Tan, Ohtake; Koji Kato, Waki; Junichi Imuta, Ohtake; Noriaki Kihara, Iwakuni, all of Japan

[73] Assignee: Mitsui Petrochemical Industries, Ltd., Tokyo, Japan

[21] Appl. No.: 138,076

[22] Filed: Dec. 28, 1987

[30] Foreign Application Priority Data

Dec. 26, 1986 [JP] Japan ................................. 61-308538

[51] Int. Cl.$^4$ ................ C07C 149/437; C07C 149/243
[52] U.S. Cl. .................................... 560/251; 548/342; 560/248; 564/104
[58] Field of Search ......................... 560/251; 564/104

[56] References Cited

U.S. PATENT DOCUMENTS 4,066,759 1/1978 Okamoto et al. ............... 560/251 X

*Primary Examiner*—Vivian Garner
*Attorney, Agent, or Firm*—Sherman & Shalloway

[57] ABSTRACT

Disclosed are alpha-acyloxyketone derivatives which are useful as intermediates for production of N-cyano-N'-methyl-N''-[2-{(5-methyl-1H-imidazol-4-yl)methyl-thio}ethyl]guanidine (common name: Cimetidine; Cimetidine applies hereinafter) and Cimetidine-related compounds which have an action of controlling secretion of gastric acid and are useful as a drug for treating gastric ulcer.

7 Claims, No Drawings

ALPHA-ACYLOXYKETONE DERIVATIVES

BACKGROUND OF THE INVENTION

1. Field of the Invention

This invention relates to alpha-acyloxyketones which are useful as intermediates for production of N-cyano-N'-methyl-N''-[2-{(5-methyl-1H-imidazol-4-yl)methylthio}ethyl]-guanidine (common name: Cimetidine) and Cimetidine-related compounds which are useful as pharmaceuticals, particularly a drug for treating gastric ulcer.

2. Description of the Prior Art

Some processes have previously been proposed for the production of Cimetidine or Cimetidine-related compounds (see, for example, Japanese Laid-Open Patent Publications Nos. 75574/1974 and 125074/1976. These processes, however, have the defect of requiring a high cost of production because they use expensive imidazole derivatives as starting materials and go through many reaction steps.

SUMMARY OF THE INVENTION

The present invention made extensive investigations in order to develop a novel process for producing imidazole derivatives which is free from the above defect of the conventional processes, and found in the course of such investigations that the above defect can be eliminated by using specific novel alpha-acyloxyketone derivatives. The present inventors specifically found that Cimetidine or Cimetidine-related compounds can be produced economically by using these novel compounds which can be obtained in high yields at low costs, and forming an imidazole ring in the final step. This finding has led to the present invention.

Thus, according to this invention, there is provided a novel alpha-acyloxyketone derivative represented by the following general formula (I)

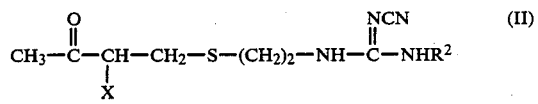

wherein $R^1$ represents a lower aliphatic acyl group, and $R^2$ represents a lower alkyl group, which is useful as an intermediate for production of Cimetidine or Cimetidine-related compounds useful as a gastric ulcer treating agent.

DETAILED DESCRIPTION OF THE INVENTION

In formula (I) representing the alpha-acyloxyketone derivatives, the lower aliphatic acyl group for $R^1$ may be, for example, formyl, acetyl, propionyl, butyryl and isobutyryl groups. The acetyl or formyl group is preferred. The formyl group is especially preferred. Examples of the lower alkyl group for $R^2$ are methyl, ethyl, n-propyl, isopropyl, n-butyl, sec-butyl and isobutyl groups. Preferably, $R^2$ is a methyl group.

The alpha-acyloxyketone derivatives of formula (I) can be obtained in high yields and at low cost by reacting an alpha-haloketone derivative represented by the formula (II)

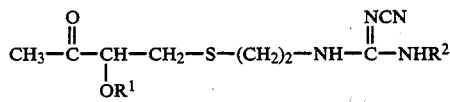

wherein X represents a chlorine or bromine atom, and $R^2$ represents a lower alkyl group, with an anhydrous lower fatty acid salt such as sodium formate, sodium acetate, potassium formate and potassium acetate. Usually, the reaction is carried out in a solventl, for example, a lower alcohol such as methanol or ethanol, or an amide such as formamide, N,N-dimethylformamide or N-methylformamide. The anhydrous lower fatty acid salt is used in an amount of 1 to 10 moles per mole of the compound of formula (II), and the reaction is carried out at a temperature of from −20° to 150° C., preferably from 0° to 5° C., and completed in 0.1 to 10 hours. After the reaction, the desired product can be obtained by treating the reaction mixture in a customary manner.

The compounds provided by this invention are useful as intermediates for the production of Cimetidine and related compounds. Specifically, the compound of formula (I) provided by this invention is reacted with a formic acid derivative and an ammonium salt to give Cimetidine or its related compound represented by the following formula (III)

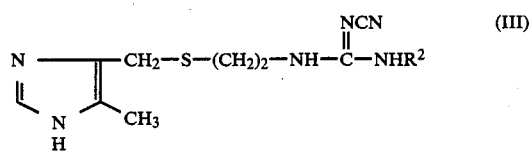

Examples of the formic acid derivative used in this reaction include formic acid esters such as methyl formate, ethyl formate, n-propyl formate, isopropyl formate, n-butyl formate and phenyl formate, ortho-formic acid esters such as methyl ortho-formate, ethyl ortho-formate and phenyl ortho-formate, formamidines such as acetic acid formamidine; and imide acid derivatives such as formamide acid methylhydrochloride. Of these orthoformic acid esters are preferred, and methyl orthoformate is especially preferred. Examples of the ammonium salt include organic or inorganic ammonium salts such as ammonium formate, ammonium acetate, ammonium propionate, ammonium benzoate, and ammonium carbonate. Aliphatic organic acid ammonium salts such as ammonium formate are particularly preferred.

The amounts of the formic acid derivative and the ammonium salt are usually both 1 to 100 moles, preferably 2 to 20 moles, per mole of the alpha-acyloxyketone derivative of formula (I). The reaction may be carried out in the absence of solvent, but the use of a solvent is preferred. The solvent may include, for example, alcohols such as methanol, ethanol, n-propanol and isopropanol, ethers such as diethyl ether, dioxane and tetrahydrofuran and aliphatic amides such as N,N-dimethylformamide, N,N-diethylformamide, formamide and acetamide. The amount of the solvent used is 0.5 to 100 parts by weight, preferably 2 to 50 parts by weight, per part by weight of alpha-acyloxyketone derivative of formula (I). The reaction temperature is 0° to 150° C., preferably 40° to 110° C., and the reaction time is 0.1 to 40 hours, preferably 0.5 to 20 hours. After the reaction, the solvent is evaporated from the reaction mixture, and the residue is purified by using general purifying means such as recrystallization and chromatography to give Cimetidine or its related compound represented by formula (III).

EXAMPLE 1

Production of N-{2-(2-formyloxy-3-oxobutylthio)ethyl}-N'-cyano-N''-methylguanidine 131 mg of N-{2-(2-chloro-3-oxobytylthio)ethyl}-N'-cyano-N''-methylguanidine and 68 mg of sodium formate were dissolved in 2.5 ml of formamide and reacted at room temperature for 5 hours. After the reaction, formamide was removed under reduced pressure, and the residue was chromatographed on a column of silica gel (eluent: chloroform/methanol=7/1) to give the desired product (yield 54%) as a colorless liquid.

$^1$H-NMR Spectrum (CDCl$_3$; ppm)

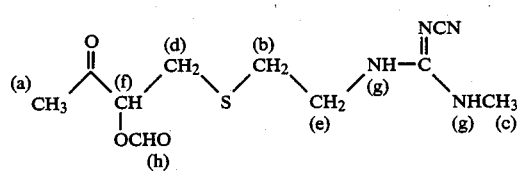

(a) 2.25 (3H, s)
(b) 2.85 (2H, m)
(c) 2.90 (3H, d, J=5.4 Hz)
(d) 3.00 (2H, m)
(e) 3.42 (2H, m)
(f) 5.35 (1H, dd, J=5.4 and 7.2 Hz)
(g) 6.42–6.84 (2H, m)

EXAMPLE 2

Example 1 was repeated except that 84 mg of potassium formate was used instead of 68 mg of sodium formate. The desired product was obtained in a yield of 52%.

EXAMPLE 3

Example 1 was repeated except that 2.5 ml of N-methylformamide was used instead of 2.5 ml of formamide, and the reaction was carried out at 50° C. for 1 hour. The desired product was obtained in a yield of 48%.

EXAMPLE 4

Production of N-{2-(2-acetoxy-3-oxobutylthio)ethyl}-N'-cyano-N''-methylguanidine A 50 ml two-necked flask was charged with 0.64 g of the same N-{2-(2-chloro-3-oxobutylthio)ethyl}-N'-cyano-N''-methylguanidine as used in Example 1, 10 ml of methanol, and 0.31 g of anhydrous sodium acetate, and the mixture was stirred at room temperature for 8 hours. Methanol was evaporated under reduced pressure, and water was added to the residue. The mixture was extracted with ethyl acetate and then dried over anhydrous magnesium sulfate. Ethyl acetate was evaporated under reduced pressure to give 0.57 g (yield 82%) of the desired product as a brown liquid.

$^1$H-NMR spectrum (CDCl$_3$; ppm):

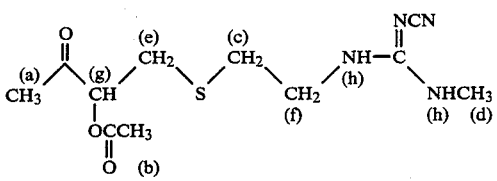

(a) or (b) 2.20 (3H, s)
(a) or (b) 2.27 (3H, s)
(c) 2.80 (2H, m)
(d) 2.86 (3H, d, J=5.4 Hz)
(e) 3.00 (2H, m)
(f) 3.42 (2H, m)
(g) 5.26 (1H, dd, J=5.4 and 7.2 Hz)
(h) 6.50–6.88 (2H, m)

REFERENTIAL EXAMPLE 1

Production of Cimetidine 136 mg of N-{2-(2-formyloxy-3-oxobutylthio)ethyl}-N'-cyano-N''-methylguanidine and 530 mg of methyl orthoformate were dissolved in 2.5 m; of formamide, and 320 mg of ammonium formate was added. The mixture was stirred at 100° C. for 2 hours. Formamide was evaporated from the reaction mixture under reduced pressure. The residue was chromatographed on a column of silica gel (eluent: chloroform/methanol=4/1), and then recrystallized from isopropanol to give 71 mg (yield 56%) of the desired product (Cimetidine) as white crystals.

REFERENTIAL EXAMPLE 2

Production of N-cyano-N'-methyl-N''-[2-{(5-methyl-1H-imidazol-4-yl)methylthio}ethyl]guanidine 155 mg of N-{2-(2-acetoxy-3-oxobutylthio)ethyl-}-N'-cyano-N''-methylguanidine and 290 mg of methyl orthoformate was dissolved in 2.5 ml of formamide, and 170 mg of ammonium formate was added. The mixture was stirred at 100° C. for 2 hours. The reaction mixture was treated as in Referential Example 1 to give 36 mg (yield 26%) of the desired product as white crystals.

What is claimed is:
1. An alpha-acyloxyketone derivative represented by the formula (I)

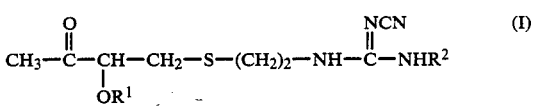

wherein R$^1$ represents a lower aliphatic acyl group, and R$^2$ represents a lower alkyl group having 1–4 carbon atoms.

2. The alpha-acyloxyketone derivative of claim 1 in which the lower aliphatic acyl group R$^1$ is a formyl, acetyl, propionyl, butyryl, or isobutyryl group.

3. The alpha-acyloxyketone derivative of claim 1 in which the lower aliphatic acyl group R$^1$ is an acetyl or formyl group.

4. The alpha-acyloxyketone derivative of claim 1 in which the lower aliphatic acyl group R$^1$ is a formyl group.

5. The alpha-acyloxyketone derivative of claim 1 in which the lower alkyl group R$^2$ is a methyl group.

6. N-(2-(2-formyloxy-3-oxobutylthio)ethyl)-N'-cyano-N''-methylguanidine.

7. N-(2-(2-acetoxy-3-oxobutylthio)ethyl)-N'-cyano-N''-methylguanidine.

* * * * *